United States Patent [19]

Moore

[11] 4,177,266

[45] Dec. 4, 1979

[54] PAIN RELIEF COMPOSITION AND METHOD OF PREPARING SAME

[75] Inventor: Mary A. Moore, Carlisle, Ky.

[73] Assignee: James Richard Bean, Laurel, Md.

[21] Appl. No.: 167

[22] Filed: Jan. 2, 1979

[51] Int. Cl.² ............................................. A61K 35/78
[52] U.S. Cl. .................................................... 424/195
[58] Field of Search ........................................ 424/195

[56] References Cited

U.S. PATENT DOCUMENTS 180,303   7/1876   Woods .................................. 424/195

OTHER PUBLICATIONS

Potter's Cyclopaedia of Botanical Drugs & Preparations, published by Potter & Clarke, Ltd., London (1900), pp. 277–278, 381–382 and 390–391.

*Primary Examiner*—Donald B. Moyer
*Attorney, Agent, or Firm*—Morton J. Rosenberg

[57] ABSTRACT

A pain relief composition and method of preparing such for producing a therapeutic composition for topical application to the skin to provide symptomatic pain relief from a number of conditions such as arthritis. The pain relief composition is prepared from roots of the family of Burdock plants and in particular from at least one of the species *Arctium lappa* as *Arctium minus* in combination with roots of the Phytolacca family and in particular the species *Phytolacca americana*. The combination of roots are inserted into a receptacle containing water. The initial mixture is heated until boiling occurs and the mixture is continually boiled for a predetermined time interval until a coloration change of the substantially transparent water is seen to occur. There is formed a substantially darkened gray colored suspension which has found to include an extract of the combination of the Phytolacca and Burdock roots with some remaining extraneous bulk material. The suspension is cooled by exposing it to the atmosphere until room temperature is achieved. A predetermined quantity of isopropyl alcohol is stirred or otherwise mixed into the aqueous suspension subsequent to the bulk material being removed therefrom. The resulting pain relief composition is then available for external application to the skin of a user.

10 Claims, No Drawings

PAIN RELIEF COMPOSITION AND METHOD OF PREPARING SAME

BACKGROUND OF THE INVENTION

1. Field of the Invention

This invention relates to pain relief compositions and methods of preparing same. In particular, this invention relates to pain relief compositions utilizing extracts of the roots obtained from the combination of the Burdock and Phytolacca families. Still further, this invention pertains to pain relief compositions utilizing extracts of *Phytolacca americana* in combination with at least one of the group obtained from *Arctium lappa* or *Arctium minus*. More in particular, this invention pertains to the heating of roots of Burdock and Phytolacca in an aqueous solution to form a suspension. Still further, this invention relates to a pain relief composition where isopropyl alcohol is added to the combination of Burdock and Phytolacca roots to produce a composition applicable for external use on the skin of a user in the area where pain is detected from arthritic conditions.

2. Prior Art

There are a number of prior compositions which are utilized to aid in minimizing pain due to arthritic conditions. However, it is believed that such compositions forming a group of internally as well as externally taken pain relief substances produce only modest successes in relieving symptomatic pains caused by such arthritic conditions.

The best prior art known to the applicant is formed in Potter's Cyclopedia of Botanical Drugs and Preparations, Published by Potter & Clarke (1900), pgs. 277-278, 381-382, and 390-391. In this prior art reference, there does not appear to be any composition or method of preparing a pain relief composition as is herein described applicable to external application on the skin of the user. In particular, this prior art reference calls for Poke Root to be emetic and cathartic which implies the ingestion of this species of the Phytolacca root.

Another prior art reference is U.S. Pat. No. 180,303, which includes extracts of yellow dock and poke root and apparently is used for the treatment of hog cholera. However, the reference prior art is directed to the ingestion of compositions utilizing such roots and not to the preparation of a composition for external skin application.

SUMMARY OF THE INVENTION

A pain relief composition prepared by the process which comprises establishing a predetermined quantity of roots from the genus Phytolacca and Burdock in an aqueous environment to form an initial mixture. The initial mixture is heated for a predetermined time interval to form a suspension which includes an extract of a combination of the Phytolacca and Burdock with a remaining bulk material. The suspension is then cooled and the bulk material is removed. Subsequently, a predetermined quantity of isopropyl alcohol is mixed with the suspension.

It is therefore the object of this invention to provide a therapeutic composition useful in the symptomatic treatment of arthritis.

It is the further object of the invention to provide a pain relief composition which utilizes the extract of the Phytolacca and Burdock to provide symptomatic relief of the pain of arthritis conditions.

DESCRIPTION OF THE PREFERRED EMBODIMENTS

Referring now to the inventive concept, there is provided a pain relief composition and method of preparing same for external application to the epidermis for relieving pain generally associated with a number of conditions including arthritis in human beings. The pain relief composition as provided in following paragraphs, is topically applied in the area of detected pain. The pain relief composition is rubbed or otherwise applied to the external surface of the skin and has been found effective for reducing the swelling and pain associated with arthritis. The pain relief composition as herein described is for external skin application only and is not directed to a composition which is to be ingested by mammals.

Initially, a quantity of roots from the Phytolacca family of plants are harvested. The particular species of Phytolacca found useful for the subject composition is *Phytolacca americana* (having a common name Pokeberry or Pokeweed). Additionally, a quantity of roots from the Burdock family (genus Arctium) are harvested. The particular species of Burdock used in the subject composition is at least one from the group of *Arctium lappa* (Great Burdock) or *Arctium minus* (Common Burdock). The roots of the Burdock and the Phytolacca are removed from the remaining leafy portion of the plants and cleansed in an aqueous solution or in some like solution not important to the inventive concept as is herein described, with the exception that the roots at the termination of the cleansing process are substantially free of dirt or other organic extraneous material. The combination of Phytolacca and Burdock is provided in approximately a 1.0:1.0 ratio by weight of each to the other.

The predetermined quantity of Phytolacca and Burdock is incorporated into an aqueous environment to form an initial mixture. The initial mixture defining the predetermined quantity of roots of the Burdock and Phytolacca in water is placed in a container for subsequent heating at approximately 1.0 atmospheres of pressure. In successful applications of the method of preparing the instant pain relief composition approximately 4.0-8.0 ounces of both Burdock and Phytolacca root were used in conjunction with approximately 1.0 gallon of water.

The initial mixture is then heated for a predetermined time interval to form a suspension which includes an extract of a combination of the root Phytolacca and Burdock as well as some remaining bulk material which is generally fibrous in nature and provides extraneous material which is to be later removed from the suspension.

The step of heating the initial mixture includes establishing an elevated temperature of the initial mixture approximately 100° C. (212° F.) of the initial mixture for a predetermined time. At this temperature, the initial mixture is found to exhibit boiling properties and the boiling mixture is maintained at the elevated temperature for a time interval defined by a coloration change of the suspension. After approximately one hour, it has been found that the suspension attains a darkened gray coloration. This is in opposition to the relatively transparent color of the aqueous portion of the initial mixture prior to the heating step.

Subsequent to the heating of the initial mixture for the predetermined time interval, a suspension including an extract of the combination of the root Phytolacca and Burdock is provided in the container. Additionally, there is also seen a remaining bulk material generally fibrous in nature and clearly discernable from the suspension.

The aqueous suspension is then cooled by convective cooling and in particular, may be cooled by natural convection. Subsequent to the cooling step, the bulk material is removed from the aqueous suspension by passing the total mixture through a screen mesh where the bulk material is thus separated from the aqueous suspension. When natural convection is utilized as the cooling heat transport medium, a time lapse in the cooling step up to twenty-four hours may be found in order to allow natural convection transport to reduce the temperature of the suspension to room temperature approximately 70° F.

The step of cooling the aqueous suspension is then followed by the step of incorporating a predetermined quantity of isopropyl alcohol to the remaining aqueous suspension and such is stirred to form a final suspension phase of the pain relief composition. Approximately one part by liquid volume of isopropyl alcohol to eight parts by liquid volume of the aqueous suspension is utilized to form the final pain relief composition of the subject inventive concept.

In this manner, there is provided a pain relief composition for topical application comprising a therapeutically effective combination extract including a predetermined concentration of root Phytolacca and Burdock. This therapeutic composition has been found highly effective for the symptomatic relief of the pain of arthritis.

An embodiment of the preferred pain relief composition is provided by establishing a predetermined quantity of *Phytolacca americana* root in an aqueous base to form an initial mixture. As in the previously described embodiment, the root of *Phytolacca americana* is initially harvested and the root of the plant is severed from the remaining portions of the plant. The root is inserted into a receptacle having an aqueous predetermined volume and raised to an elevated temperature approximating 100° C. (212° F.) to initiate a boiling or heating period.

The initial mixture formed of the roots of the Phytolacca is heated for a predetermined time interval and subsequently forms a suspension which includes an extract of the root Phytolacca and remaining extraneous bulk material which is visually discernable.

The initial mixture is boiled or otherwise heated in the receptacle until a coloration change from substantially a transparent color to a light gray coloration is seen. The colored suspension is then cooled through natural convection or some other technique not important to the inventive concept until room temperature approximately 70° F. is attained. At the end of the cooling phase in the preparation of the pain relief composition, the bulk material is then removed and a predetermined quantity of isopropyl alcohol is added to the suspension. The isopropyl alcohol is stirred into the suspension in the final phase of the preparation of the pain relief composition.

Thus, there is provided a pain relief composition for topical application comprising a therapeutically effective extract obtained from the root Phytolacca.

EXAMPLE

Approximately twenty plants of the root Phytolacca (species *Phytolacca americana*) and twenty plants of Burdock (*Arctium minus*) were harvested. The root portion of the plants were severed from the remaining leafy sections of the plants. The roots were weighed and found to be in approximately a 1.0:1.0 weigh ratio each to the other. The roots were then inserted into a receptacle containing 1.0 gallons of water. The weight of the Burdock root was found to be approximately 6.0 ounces and the weight of the root Phytolacca approximately 5.0 ounces.

The roots and the water within the receptacle were heated to approximately 100° C. until boiling occurred. Prior to boiling, the water in the initial mixture containing the roots and the water was found to be transparent. During the boiling, the water was found to change to a darkened gray color and the receptacle was removed from the heating medium. The receptacle was exposed to the external environment at approximately 1.0 atmospheres of pressure and natural convection cooling occurred. The receptacle remained open to the atmosphere for approximately twelve hours until the temperature of the suspension reached room temperature approximating 70° F.

Bulk material of a fibrous nature was seen in the overall suspension and the bulk material was strained from the suspension by passing the entire receptacle contents through a mesh screen. The final suspension minus the bulk material had approximately 1.0 pint of isopropyl alcohol added to it and stirred.

Topical application of the final suspension to a local pain site area caused by arthritis was found to reduce the symptomatic pain and apparently aided in the reducing of swelling in the pain area.

Other embodiments and modifications will readily come to those of ordinary skill in the art having the benefit of the teachings presented in the foregoing description. It is therefore to be understood that this invention is not to be limited thereto and that said modification and embodiments are intended to be included within the scope of the appended claims.

What is claimed is:

1. A pain relief composition prepared by the process comprising:
    (a) establishing a predetermined quantity of roots from the genus Phytolacca and Burdock in an aqueous environment to form an initial mixture;
    (b) heating said initial mixture for a predetermined time interval to form a suspension including an extract of a combination of said Phytolacca, Burdock and remaining bulk material thereof;
    (c) cooling said aqueous suspension; and,
    (d) incorporating a predetermined quantity of isopropyl alcohol to said aqueous suspension.

2. The pain relief composition preparation process as recited in claim 1 where the step of establishing includes the step of providing approximately 1.0 part by weight of said root Phytolacca to approximately 1.0 part by weight of said Burdock to form said predetermined quantity.

3. The pain relief composition preparation process as recited in claim 1 where said genus Phytolacca is of the species *Phytolacca americana*.

4. The pain relief composition preparation process as recited in claim 1 where said genus Burdock is of the species *Arctium minus*.

5. The pain relief composition preparation process as recited in claim 1 where the step of heating includes the step of establishing an elevated temperature of approximately 100° C. of said initial mixture for said predetermined time interval.

6. The pain relief composition preparation process as recited in claim 5 where the step of heating includes the step of maintaining said elevated temperature for said time interval defining a coloration change of said suspension.

7. The pain relief composition preparation process as recited in claim 1 where said step of cooling includes the step of convectively cooling said suspension.

8. The pain relief composition preparation process as recited in claim 7 where said convective cooling is natural convection.

9. The pain relief composition as recited in claim 1 where the step of cooling is followed by the step of removing said bulk material from said aqueous suspension.

10. The pain relief composition as recited in claim 1 where the step of incorporating includes the step of adding approximately 1 part by liquid volume of said isopropyl alcohol to 8 parts by liquid volume of said aqueous suspension.

* * * * *